United States Patent [19]
Ohba et al.

[11] Patent Number: 5,798,459
[45] Date of Patent: Aug. 25, 1998

[54] SUBJECT IDENTIFICATION METHOD, APPARATUS AND SYSTEM

[75] Inventors: Ryoji Ohba, Sapporo; Yoshihito Tamanoi, Yamaguchi-ken, both of Japan

[73] Assignees: Japan as represented by President of Hokkaido University, Sapporo; Koa Oil Company, Limited, Tokyo, both of Japan

[21] Appl. No.: 716,208

[22] PCT Filed: Feb. 8, 1996

[86] PCT No.: PCT/JP96/00266

§ 371 Date: Apr. 1, 1997

§ 102(e) Date: Apr. 1, 1997

[87] PCT Pub. No.: WO96/35926

PCT Pub. Date: Nov. 14, 1996

[30] Foreign Application Priority Data

May 12, 1995 [JP] Japan .................. 7-114366

[51] Int. Cl.$^6$ .................. G08B 21/00; G06F 15/46; G06F 17/10; G05B 13/02
[52] U.S. Cl. .................. 73/587; 364/554; 364/550; 73/40.5 A; 73/660
[58] Field of Search .................. 73/40.5 A, 40.5 R, 73/587, 592, 593, 654, 660, 650; 364/148–151, 507, 550, 551.01, 554, 572, 574, 578, 724.014, 724.11

[56] References Cited

U.S. PATENT DOCUMENTS

| | | | |
|---|---|---|---|
| 4,882,668 | 11/1989 | Schmid et al. | 364/600 |
| 4,980,844 | 12/1990 | Demjanenlco et al. | 364/550 |
| 5,343,420 | 8/1994 | Murata et al. | 364/825 |
| 5,477,730 | 12/1995 | Carter | 73/609 |
| 5,623,402 | 4/1997 | Johnson | 364/162 |

FOREIGN PATENT DOCUMENTS

| | | |
|---|---|---|
| 59-142424 A | 8/1984 | Japan . |
| 60-123730 A | 7/1985 | Japan . |
| 60-146834 U | 9/1985 | Japan . |
| 7-43259 A | 2/1995 | Japan . |

*Primary Examiner*—Hezron E. Williams
*Assistant Examiner*—Rose M. Miller
*Attorney, Agent, or Firm*—Kubovcik & Kubovcik

[57] ABSTRACT

The present invention relates to a subject identification method which is adapted for performing an examination as to whether any change exists on a subject, or adapted for performing an estimation of a degree of the change on the subject. It is an aim that the examination and the estimation are performed with great accuracy. Residual signals are evaluated by means of letting an inverse filter interact with a standard and samples which may be out of the standard, so that a plurality of statistical variables are extracted, thereby testing or estimating as to whether a statistical significant difference exists between those two statistical variable groups.

16 Claims, 9 Drawing Sheets

SUBJECT IDENTIFICATION METHOD, APPARATUS AND SYSTEM

TECHNICAL FIELD

The present invention relates to a subject identification method, a subject identification apparatus, and a subject identification system, which are adapted for performing an examination as to whether any change exists on an subject, such as whether or not the subject is the same one or the same type of one, whether the subject is placed under the same condition, or whether the subject is in the same state, or adapted for performing an estimation of a degree of the change on the subject.

BACKGROUND ART

Hitherto, there have been proposed in various fields various schemes for detecting a malfunction or a failure of devices, products, facilities and the like.

Hereinafter, there will be explained, by way of example, a scheme in which leakage of a gas, such as inflammable gas, toxic gas and the like, or a liquid, which are treated in manufacturing devices and facilities of a gas manufacturing plant, an oil manufacturing plant and a chemical plant, is detected on the basis of a leakage signal having an ultrasonic frequency band which may emanate when the above-mentioned gas or liquid is leaked through microapertures of instruments, laying pipes or the like, for example, eroded apertures due to the aged deterioration, and the malfunction of the facilities is detected in accordance with the presence or absence of the leakage.

Hitherto, in the above-mentioned equipments and plants, as a scheme of detecting leakage of inflammable gas and toxic gas, there is generally used a concentration type gas sensor established permanently. The concentration type gas sensor adopts a scheme in which the leaked gas is only detected when it reaches a certain detected concentration level or more. Accordingly, there is a need to install the concentration type gas sensor in a place where the gas is prone to stay. However, this scheme involves such drawbacks that it is difficult to select such a place, and a detection precision varies under the influence of the direction of the wind. Specifically, in a case where a leakage occurs far from a place where the gas sensor is installed, it happens that a large amount of gas is leaked owing to a diffusion in addition to the influence of the wind until the gas concentration reaches a detection level. In view of the foregoing, in order to earlier detect a leakage with the concentration type gas sensor, there is a need to provide a lot of concentration type gas sensors.

As another technology of leakage detection, an instrument (an ultrasonic leakage detector) for catching and detecting ultrasounds, which emanate when gas is ejected through microapertures, comes onto the market. As a scheme in which the above-mentioned technology is further developed so as to detect a leakage source, Japanese Utility Model Application Laid Open Gazette No. Sho.60-146834 discloses a technology in which a paraboloidal body is partitioned with segments so that ultrasonic sensors are accommodated into the associated partitions, respectively, and a position of the leakage source is detected in accordance with a turn-on condition of the monitor lamp of the display of the associated one of the respective sensors.

However, in any types of technology mentioned above, in which ultrasounds involved in the leakage are caught, it is possible to catch the ultrasounds when there is no ultrasonic noises other than leakage sounds. Thus, those types of technology are effective only in a place having environment, which is not subjected to the ultrasonic noises, such as pipe lines installed in an uncultivated field. On the contrary, there will exist a limitless number of ultrasonic noises on the plants and the manufacturing devices which need a leakage sensing technology. Those ultrasonic noises are as follows: leakage sounds of normal steam emanated from valve stems, such as a trip & throttle valve and a governing valve, which constitute a pump driving steam turbine in a manufacturing device; leakage sounds of normal steam emanated from a turbine rotor shaft seal packing of the turbine; leakage sounds of normal air emanated from an air positioner constituting a control valve for controlling flow rate and a liquid level; ultrasounds of fluid emanated owing to throttling of a valve; and sliding frictional sounds of rotary machines.

Actually, since the devices generate a limitless number of ultrasounds as mentioned above in the form of environmental noises, the equipments for detecting leakage sounds of interest with adopting the above-mentioned types of technology will respond to the ultrasounds in the form of environmental noises. Thus, such equipments are not practical.

Further, as another scheme of leakage diagnosis using no ultrasounds, there has been proposed a method of detecting a leakage through monitoring changes of a sound pressure level and a level of frequency spectrum in audio-frequency band. The leakage sound of the audio-frequency band is effective for a detection method of detecting a large amount of leakage of loud noises which involve a change of a level of sound pressure. With respect to detection of a minor amount of leakage, however, the leakage sound of the audio-frequency band is prone to be affected by the environmental noises, for example, rain noises, noises of speakers in plants, noises of vehicles and airplanes, and the like, appearing in the form of disturbance which exceeds the environmental noises in the detection scheme involved in the ultrasonic frequency band.

Especially, in facilities which treat a large amount of inflammable gas such as a dangerous object, there is desired a technology in which a leakage is detected in the initial minor leakage stage before a large amount of leakage involving a loud noise, so that a serious disaster is prevented. From the point of view as mentioned above, the conventional technology as to a leakage monitor of the audio-frequency band, which is weak in the noises, is not preferable.

In view of the foregoing, as a scheme in which even under an environment such that a large noise, for example, environmental noises as mentioned above, exists, a malfunction and a failure (in case of the above, a leakage) can be detected, the applicant of the present application has proposed (in Japanese Patent Application Laid Open Gazette No. Hei.7-43259) a scheme in which an inverse filter to a signal derived at the normal state (existing noises) is previously produced, and a signal is derived at the time point when it is considered that the malfunction or failure perhaps occurs, so that the inverse filter acts on the signal thus derived to form a residual signal in which components including noises involved in the normal state are removed, and thus the presence or absence of a malfunction and a failure is determined on the basis of the residual signal. This scheme is very excellent as a scheme of removing regular noises.

On the contrary, as will be described hereinafter, it happens that the phenomenon due to the malfunction or failure and the phenomenon in the normal state resemble each other very much.

Now, let us consider, for example, such a case that leakages of inflammable gas or toxic gas through gas laying pipes in a plant are detected. In such a plant, usually, there are provided a large number of steam pipings for a power or a heater around the gas pipings. Each of the steam pipings is provided with a steam trap for discharging intentionally intermittently the steam to discharge water which would be brought by condensation of the steam inside the steam piping. The discharge of the steam through the steam trap and a leakage of gas through the eroded aperture of the gas piping resemble each other very much. In such a case, even the above-mentioned scheme is adopted to remove the influence of the noises in the normal state, such as the environmental noises, for example, the discharge of the steam through the above-mentioned steam trap would be determined as the abnormal state. Thus, it happens that erroneous detection cannot be avoided.

In view of the foregoing, it is an object of the present invention to provide a subject identification method capable of detecting as to whether a change occurs on the subject, or performing a presumption of a degree of the change with great accuracy, a subject identification apparatus suitable for implementation of the above-mentioned method, and a subject identification system in which the above-mentioned method is applied.

DISCLOSURE OF THE INVENTION

According to the present invention, in order to attain the object of the invention mentioned above, there is provided a subject identification method comprising:

(1-1) a first step of obtaining a plurality of first time sequential signals each carrying a predetermined physical amount from a predetermined first subject;

(1-2) a second step of producing an inverse filter on the basis of at least one of said plurality of first time sequential signals;

(1-3) a third step of evaluating a plurality of first residual signals by means of letting said filter interact with at least part of said plurality of first time sequential signals;

(1-4) a fourth step of evaluating a plurality of predetermined statistical variables on the basis of said plurality of first residual signals;

(1-5) a fifth step of obtaining a plurality of second time sequential signals each carrying said predetermined physical amount from a predetermined second subject;

(1-6) a sixth step of evaluating a plurality of second residual signals by means of letting said inverse filter interact with said plurality of second time sequential signals;

(1-7) a seventh step of evaluating said plurality of predetermined statistical variables on the basis of said plurality of second residual signals; and (1-8) an eighth step of presuming or testing a statistical difference between the plurality of predetermined statistical variables evaluated in the fourth step and the plurality of predetermined statistical variables evaluated in the seventh step.

In the subject identification method as mentioned above, it is acceptable that the fourth step (1-4) has:

a step (1-4-1) of evaluating power spectra of a frequency band of at least part of said plurality of first residual signals; and an additional step (1-4-2) of evaluating the predetermined statistical variables on the basis of the power spectra, and the seventh step (1-7) has:

a step (1-7-1) of evaluating power spectra of a frequency band of at least part of said plurality of second residual signals; and an additional step (1-7-2) of evaluating the predetermined statistical variables on the basis of the power spectra.

Further, in the subject identification method as mentioned above, the eighth step (1-8) is to presume or test a difference in population variances and/or population means.

Incidentally, in the subject identification method as mentioned above, it is acceptable that the first and second subjects are the same or same type of subject.

In the subject identification method according to the present invention, examples of the first and second subjects, and the presumption and the test will be described hereinafter.

(a) A standard one or a plurality of pieces of a number of same type of products (for example, a number of motors manufactured with the same standard) are defined as the first subject, and an inverse filter is produced beforehand on the basis of signals carrying the physical amount (e.g. torque of motors, motor sounds and the like) related to the standard products. In this condition, it is tested as to whether the other numerous same type of products are acceptable or defective.

(b) A certain apparatus is defined as the first subject and the second subject, and an inverse filter is produced beforehand on the basis of signals obtained through picking up the physical amount (e.g. a vibration of the apparatus, the operating sounds and the like) related to the apparatus when it is operating normally. In this condition, it is presumed how degree a change occurs as compared with the normal operation of the apparatus (e.g. how degree the operating sounds approach the abnormal state). Alternatively, it is tested as to whether the apparatus is normal or abnormal.

(c) When materials and the like are broken, it is known that a weak sound emanates prior to the destroy (a so-called acoustic emission). One including an environment in which such materials is placed are defined as the first subject and the second subject, and an inverse filter is produced beforehand on the basis of the environment noises involved in the normality of the materials and the like. In this condition, the significant level as to the destroy of the materials and the like is presumed through the acoustic emission.

(d) For example, the whole environment (e.g. noises) of a certain plant is defined as the first subject and the second subject, but not for a specified device or facilities, and an inverse filter is produced beforehand on the basis of the usual environment of the plant of the materials and the like. In this condition, it is tested whether the abnormality occurs on the environment of the plant.

It is noted that the above-mentioned "predetermined physical amount" is also not restricted to a specified physical amount. By way of example, in a case where a rotary machine is defined as the subject, various physical amounts, such as a vibration of the case of the rotary machine, sounds emanated due to the vibration, and run-out of the rotary shaft of the rotary machine, can be selected as the above-mentioned "predetermined physical amount".

Further, the above-mentioned "predetermined statistical variable" is also not restricted to a specific statistical variable. It is acceptable to adopt any amounts as the predetermined statistical variable, if they represent the features of the residual signals. It is possible to adopt various statistical variables, for example, a means value of the residual signals, a variance of the residual signals, a variance of power spectra of the residual signals, (maximum-minimum), the maximum and the like, in accordance with a property of the residual signals.

According to the present invention, there is provided a first subject identification apparatus comprising:

(2-1) a sensor for obtaining time sequential signals each carrying a predetermined physical amount by means of measuring the predetermined physical amount of a subject;

(2-2) an inverse filter producing means for producing an inverse filter on the basis of the time sequential signals obtained by said sensor;

(2-3) a variable operating means for evaluating residual signals by means of letting said inverse filter produced by said inverse filter producing means interact with the plurality of time sequential signals obtained by the sensor, and evaluating predetermined statistical variables on the basis of the residual signals;

(2-4) a storage means for storing the predetermined statistical variables evaluated by said variable operating means; and (2-5) a statistical means for presuming or testing a statistical difference between groups in which the plurality of predetermined statistical variables stored in said storage means are partitioned into at least two groups.

The above-mentioned first subject identification apparatus has an arrangement in which the inverse filter means (2-2) is incorporated thereinto, and both two statistical variable groups, which are objects of the presumption or test of the statistical difference, are fetched in the apparatus. However, it is acceptable that the inverse filter and one of the statistical variable groups, that is, the reference statistical variable group, are evaluated beforehand and incorporated into the apparatus.

The subject identification apparatus thus constructed comprising:

(3-1) a first storage means for storing an inverse filter and a plurality of predetermined statistical variables;

(3-2) a sensor for obtaining time sequential signals each carrying a predetermined physical amount by means of measuring the predetermined physical amount of a subject;

(3-3) a variable operating means for evaluating residual signals by means of letting said inverse filter stored in said first storage means interact with the time sequential signals obtained by the sensor, and evaluating the predetermined statistical variables on the basis of the residual signals;

(3-4) a second storage means for storing the predetermined statistical variables evaluated by said variable operating means; and (3-5) a statistical means for presuming or testing a statistical difference between the plurality of predetermined statistical variables stored in said first storage means and the plurality of predetermined statistical variables stored in said second storage means.

Further, according to the present invention, there is provided a subject identification system comprising:

(4-1) at least one sound pressure sensor disposed at a place having a predetermined position relation with respect to a subject;

(4-2) a sensor attitude control apparatus for causing said sound pressure sensor to turn various directions; and (4-3) a monitor apparatus having an inverse filter producing means for producing an inverse filter on the basis of sound signals obtained by said sound pressure sensor, a variable operating means for evaluating residual signals by means of letting said inverse filter produced by said inverse filter producing means interact with the plurality of sound signals obtained by said sound pressure sensor, and evaluating predetermined statistical variables on the basis of the residual signals, a storage means for storing the predetermined statistical variables evaluated by said variable operating means, and a statistical means for presuming or testing a statistical difference between groups in which the plurality of predetermined statistical variables stored in said storage means are partitioned into at least two groups.

The arbitrary time sequential signal can be regarded as an output derived when a white noise is fed to a suitable linear system. It is referred to as a linear prediction analysis that a linear system is determined on the basis of a given time sequence. In this respect, the established technique exists. Usually, as one evaluated in accordance with such a technique, there is known an autoregressive model (AR model). According to the AR model, when the time sequential signals subjected to a sampling process and a discrete-value process are expressed by $X(n)$, $n=1, 2, \ldots$, the signal $X(n)$ at the time point n-th is determined in accordance with data on M pieces of time point before n-th as follows.

$$X(n) = - \sum_{k=1}^{M} A_k X(n-k) + e(n) \tag{1}$$

Where $e(n)$ is a virtual input signal to the linear system and a white noise. When the time sequential signals are given, the associated autoregressive model is determined by evaluating a set $\{A_K\}$ of coefficients on the basis of the data.

Now, when the set $\{A_K\}$ of coefficients is determined, $Y(n)$ is defined, using the time sequential signals data $\{X(n)\}$, as follows.

$$Y(n) = - \sum_{k=1}^{M} A_k X(n-k) \tag{2}$$

From equations (1) and (2), $$X(n) - Y(n) = e(n) \tag{3}$$

The residual represents the white noise. That is, the white noise is derived through the subtraction in which from the time sequential signals data $X(n)$ at the time point n-th, the prediction value $Y(n)$ evaluated on the basis of M pieces of data before n-th is subtracted. Here, it is referred to as an inverse filter being interacted that the residual $e(n)$ is evaluated through the subtraction in which the prediction value $Y(n)$ is subtracted from the time sequential signals data $X(n)$ at the time point n-th. In this manner, if a certain time sequential signal can be represented by a suitable autoregressive model, it is possible to obtain the white noise by means of letting the inverse filter thus produced interact with the original time sequential signal. In other words, the input signal is whitened through the inverse filter. In this case, it is acceptable that the input time sequential signal is not the signal which is used in the design for the inverse filter. It is possible to obtain a whitened signal as an output if the autoregressive model is identical, that is, the input time sequential signal has the same property. On the other hand, when the property of the time sequential signal is different from that used in the design. the input signal is not whitened and thus it is impossible to obtain the white noise.

In view of the foregoing. a first time sequential signal. which carries. for example, operating sounds, vibration and the like (hereinafter. referred to as operating sounds and the like) at the time of the normality, is used to form an inverse filter. and a second time sequential signal. which carries the operating sounds and the like at an arbitrary time point. is derived so as to let the inverse filter interact with the second time sequential signal and monitor the output. whereby it is possible to detect a time sequential signal (residual signal) which is different from one obtained at the time of the normality.

One of the aspects of the present invention resides, similar to the technique disclosed in Japanese Patent Application Laid Open Gazette No. Hei. 7-43259, in the point that an inverse filter is produced beforehand on the basis of the first time sequential signal obtained from the subject device and the like in the normal state, and the residual signal is evaluated by means of letting the inverse filter interact with the second time sequential signal obtained from the subject device and the like. Hence. the residual signal is representative of the "difference" from the first time sequential signal involved in the normal state, and may be evaluated in accordance with a simple way that a linear prediction value $Y(n)$ is evaluated (the above equation (2)) by a simple weighted addition of M pieces of data on a time sequence basis and the difference is evaluated (the above equation (3)). Accordingly, a simple operation may be performed on a real time basis.

By the way, even the residual signal representative of the "difference" between the first time sequential signal and the second time sequential signal is evaluated, as an example of the steam trap as mentioned above, it happens that the "difference" does not always exist, and two objects to be distinguished from one another, for example, the normal state and the abnormal state, overlap with one another. In this case, it is sufficient that the "difference" is simply exactly evaluated.

In view of the foregoing, according to the present invention, the statistical variables are evaluated so that the statistical significant difference between statistical variable group-to-statistical variable group is presumed or tested. Thus, it is possible to perform with great accuracy the test or examination as to the existence of a difference between the first subject and the second subject, or the presumption of the degree of the difference.

As mentioned above, according to the present invention, it is possible to perform with great accuracy the test as to whether any change occurs on the subject, or the presumption of the degree of the change.

BEST MODE FOR CARRYING OUT THE INVENTION

Hereinafter, embodiments of the present invention will be explained.

Here, assuming that inflammable gas piping facilities, including an environment in which steam piping equipments and in addition background noise sources exist around the facilities, are referred to as the first subject and the second subject, there will be explained a case in which the existence of a gas leakage through apertures or cracks due to erosion or the like on the laying pipes in the inflammable gas piping facilities is tested. It is noted that since an experiment according to the inflammable gas involves danger, the experiment was carried out in accordance with such a manner that the pipe is filled with air instead of the inflammable gas and the eroded aperture is replaced by the artificial aperture. Thus, the experimental data, which will be shown hereinafter, are obtained through the experiment as mentioned above. However, as a matter of convenience of the description, an air leakage through the artificial aperture or the like is also expressed as the gas leakage.

Figure 1:
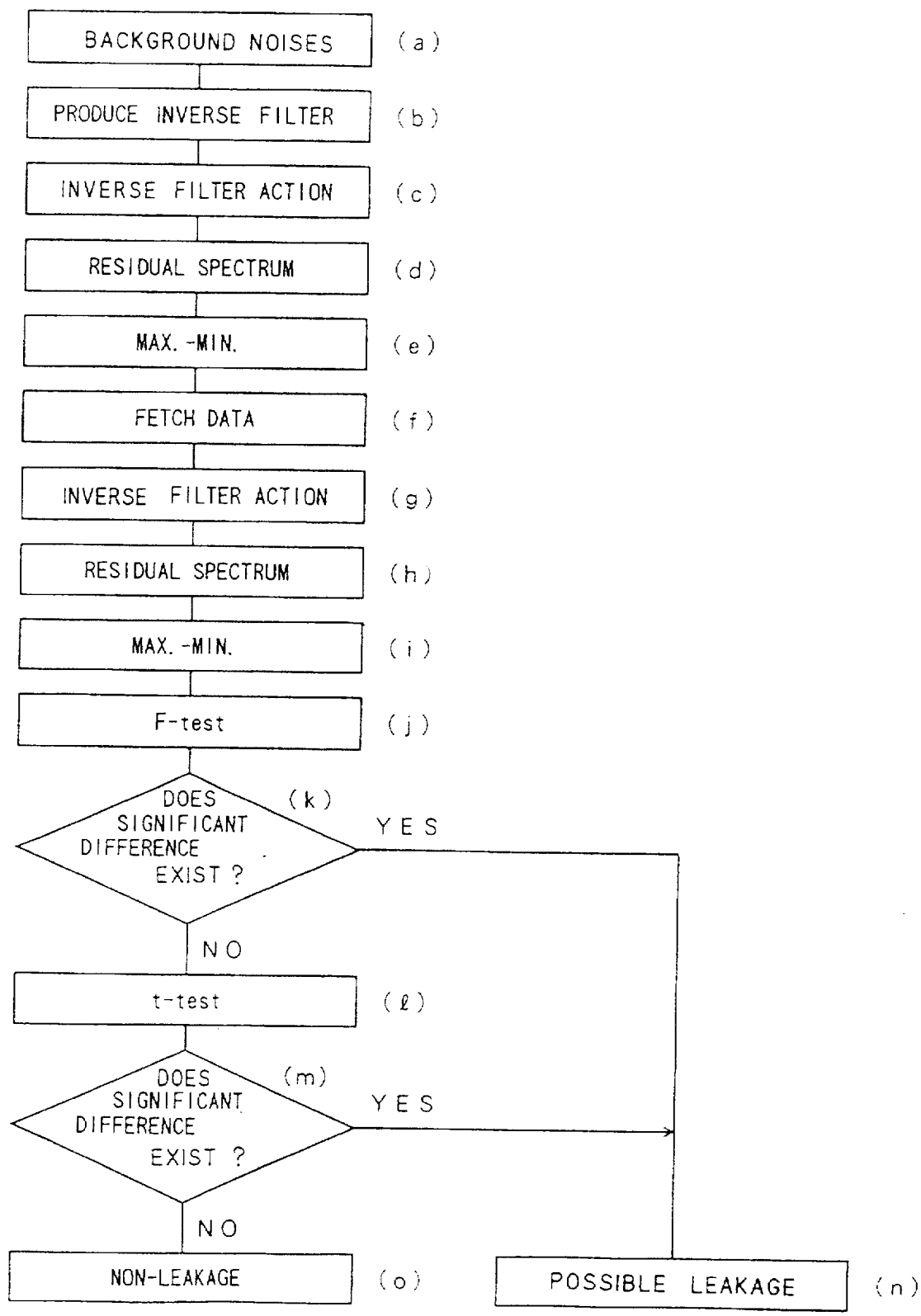
FIG. 1 is a flowchart showing one embodiment of a subject identification method according to the present invention.

FIG. 1 is a flowchart showing one embodiment of a subject identification method according to the present invention.

Referring to FIG. 1, first, in step (a), background noises are collected a plurality of number of times at the place where the inflammable gas piping facilities of interest are disposed.

Next, in step (b), an inverse filter is produced on the basis of a certain background noise signal from among a plurality of background noise signals collected. In step (c), a plurality of residual signals are evaluated by means of letting the inverse filter interact with the plurality of background noise data but the background noise data based on which the inverse filter is produced. In step (d), the power spectra of each of the plurality of residual signals is evaluated. In step (e), the maximum and the minimum of the power spectra in a predetermined frequency band are extracted so that (maximum-minimum) is evaluated by way of a predetermined statistical variable.

Next, in steps (f)–(i), sounds due to the leakage of inflammable gas through the inflammable gas piping are collected in background noises, and in a similar fashion to that of the above, (maximum-minimum) is evaluated.

Next, there is carried out a test as to whether a significant difference exists between a group of (maximum-minimum) evaluated in step (e) and a group of (maximum-minimum) evaluated in step (i).

Here, first, in step (j), a F-test is carried out. The F-test is a technique of testing as to whether a significant difference exists between variances a $\sigma_x^2$ and $\sigma_y^2$ of two statistical variable groups (here, groups of (maximum-minimum)). The F-test may be summarized as follows (cf. "LECTURES ON QUALITY CONTROL FIRST EDITION STATISTICAL METHOD" by Shigekazu Moriguti Japanese Standards Association).

(1) Set up a hypothesis $H_0: \sigma_x^2 = \sigma_y^2$ (2) Evaluate unbiased variances $V_x$ and $V_y$, of which degrees of freedom are given by $\phi_x$ and $\phi_y$, respectively.

(3) Evaluate variance ratio.
 When
  $V_x \geq V_y$, $F_0 = V_x/V_y$
  $\phi_1 = \phi_x$, $\phi_2 = \phi_y$
 When
  $V_x < V_y$, $F_0 = V_y/V_x$
  $\phi_1 = \phi_y$, $\phi_2 = \phi_x$ (4) Determination
 If $F_0 \geq F\phi_1$, $\phi_2$ (0.025), hypothesis $H_0$ is dismissed (level of significance 5%). Where $F\phi_1$, $\phi_2$ (0.025) implies that upper side probability of F-distribution of degree of freedom $(\phi_1, \phi_2)$ is 0.025.

In step (k), it is determined by the F-test whether a significant difference exists, that is, whether hypothesis $H_0$ is dismissed in the above item (4). If it is determined that the significant difference exists, that is, hypothesis $H_0$ is dismissed, the program proceeds to step (n) in which it is determined that the gas leakage is present.

Further, in step (k), when it is determined that no significant difference exists, the process goes to step (l) in which a t-test is carried out. The t-test is a technique of testing as to whether a significant difference exists between means of two statistical variable groups. The t-test may be summarized as follows (cf. "LECTURES ON QUALITY CONTROL FIRST EDITION STATISTICAL METHOD" by Shigekazu Moriguti Japanese Standards Association).

(1) Set up a hypothesis $H_0: \mu = \mu_0$ (population mean $\mu$ equals $\mu_0$)

Here, it is detected whether $\mu$ equals $\mu_0 (\mu = \mu_0)$ on a statistical basis, where mean of one of the two statistical variable groups, that is, a statistical variable group as a reference, is expressed by $\mu_0$, and the other (sample) of the two statistical variable groups is expressed by $\mu$.

(2) Evaluate mean $<x>$ of the sample and unbiased variance V.

(3) Evaluate standard variation $\sqrt{(V/N)}$ of mean $<x>$ of the sample, where N denotes a number of samples.

(4) Evaluate $t_0$ in accordance with the following equation.

$t_0 = (<x> - \mu_0)/\{\sqrt{(V/N)}\}$ (5) Determination

If $|t_0| \geq t$ (N−1, 0.05), hypothesis $H_0$ is dismissed (level of significance 5%). Where t (N−1, 0.05) implies points of both sides 5% of the t-distribution of a degree of freedom $\phi = N-1$.

In step (m), it is determined by the t-test in step (l) whether a significant difference exists, that is, whether hypothesis $H_0$ is dismissed. If it is determined that the significant difference exists, it is determined that the gas leakage is present. On the other hand, if it is determined that no significant difference exists also in the t-test, subsequently to the above-mentioned F-test, it is determined the gas leakage is absent.

Figure 2:
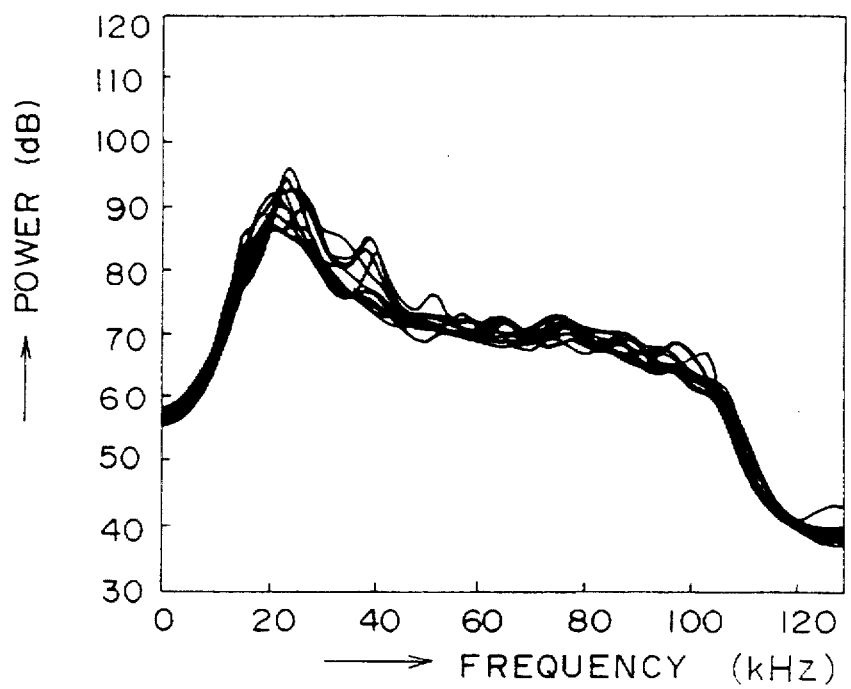
FIG. 2 is a view showing smoothed power spectra of background noises.

FIG. 2 is a view showing smoothed power spectra of background noises collected in step (a) shown in FIG. 1. In FIG. 2 and the following similar figures, the axis of abscissas and the axis of ordinates denote a frequency (k Hz) and a power (dB), respectively. Here, the collected signals interact with a band-pass filter of 20 k Hz–100K Hz.

FIG. 2 shows smoothed power spectra of background noises of each of the pauses formed through partitioning the collected noises at fixed intervals of time, at 10-pause correspondence.

Figure 3:
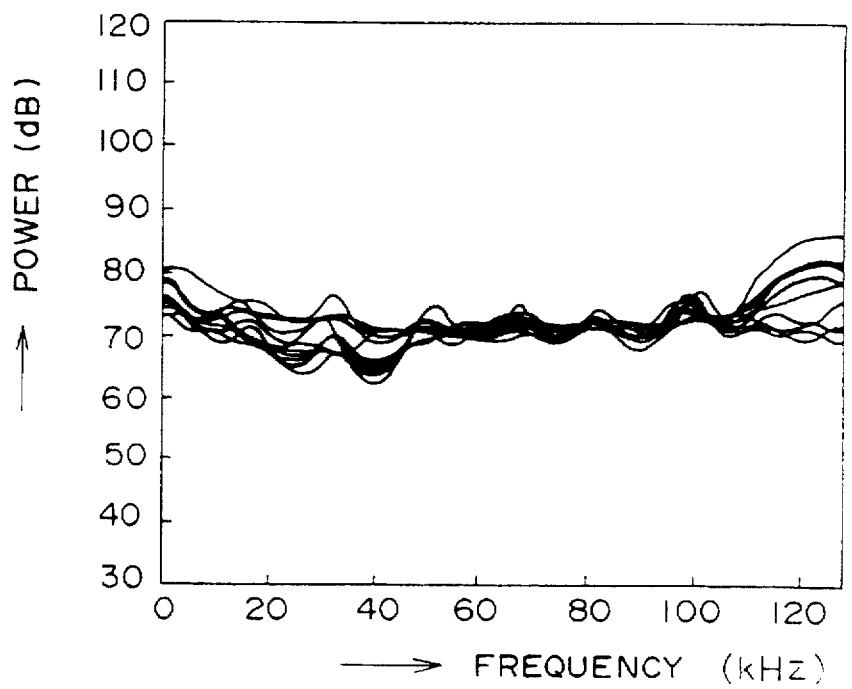
FIG. 3 is a view showing smoothed power spectra of residual signals formed by means of letting an inverse filter interact with the background noises of 10 pauses of which the power spectra are shown in FIG. 2.

FIG. 3 is a view showing smoothed power spectra of residual signals formed by means of letting an inverse filter interact with the background noises of 10 pauses of which the power spectra are shown in FIG. 2 (cf. steps (c) and (d) in FIG. 1).

Here, there is used an inverse filter produced on the basis of background noises involved in pauses collected in the same condition, which are different from the background noises involved in 10 pauses of which power spectra are shown in FIG. 2. Incidentally, it is acceptable to arrange an adaptive inverse filter based on background noises of a plurality of pauses.

As seen from FIG. 3, the background noises have been almost clearly removed.

In step (e), a difference between the maximum and the minimum of the power spectra of the residual signals in the pauses of 50 k Hz–100K Hz is extracted in the form of statistical variable.

Figure 4:
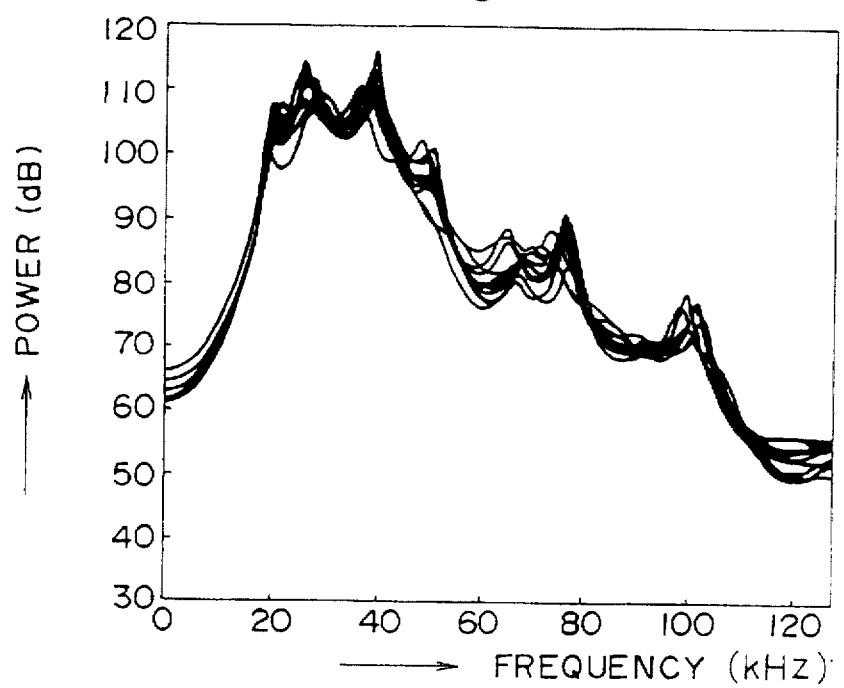
FIG. 4 is a view showing smoothed power spectra of 10 pauses of signals collected when a leakage of gas exists.
Figure 5:
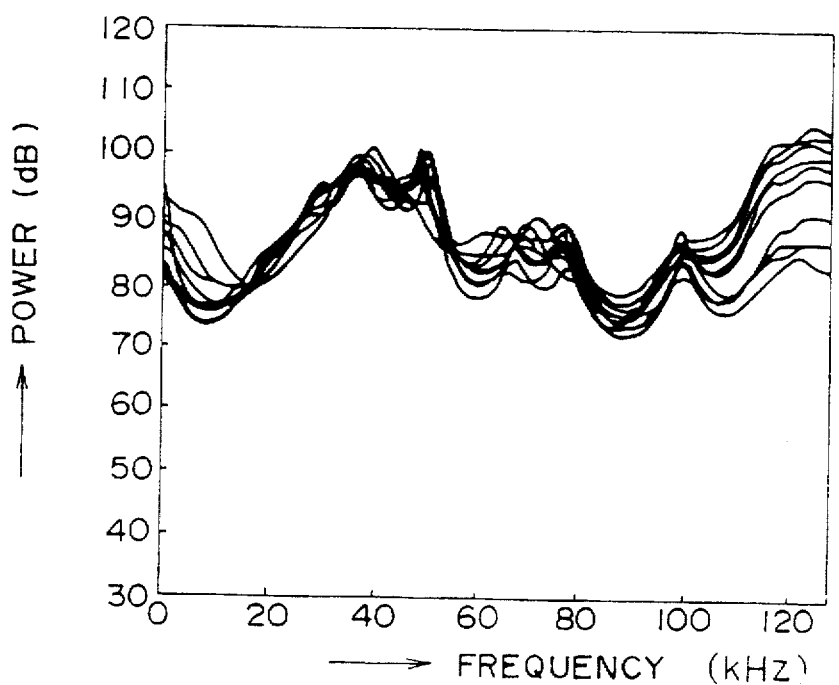
FIG. 5 is a view showing power spectra of residual signals formed by means of letting an inverse filter, which is the same as the inverse filter used in formation of the residual signals shown in FIG. 3 by means of letting the inverse filter interact with the background noises shown in FIG. 2, interact with signals of which the power spectra are shown in FIG. 4.

FIG. 4 is a view showing smoothed power spectra of 10 pauses of signals collected when a leakage of gas exists, in step (f) shown in FIG. 1. FIG. 5 is a view showing power spectra of residual signals formed by means of letting an inverse filter, which is the same as the inverse filter (produced in step (b)) used in formation of the residual signals shown in FIG. 3 by means of letting the inverse filter interact with the background noises shown in FIG. 2, interact with signals of which the power spectra are shown in FIG. 4.

In step (i), a difference between the maximum and the minimum of the power spectra of the residual signals in the pauses of 50 k Hz–100K Hz, shown in FIG. 5, is extracted in the form of statistical variable.

Figure 6:
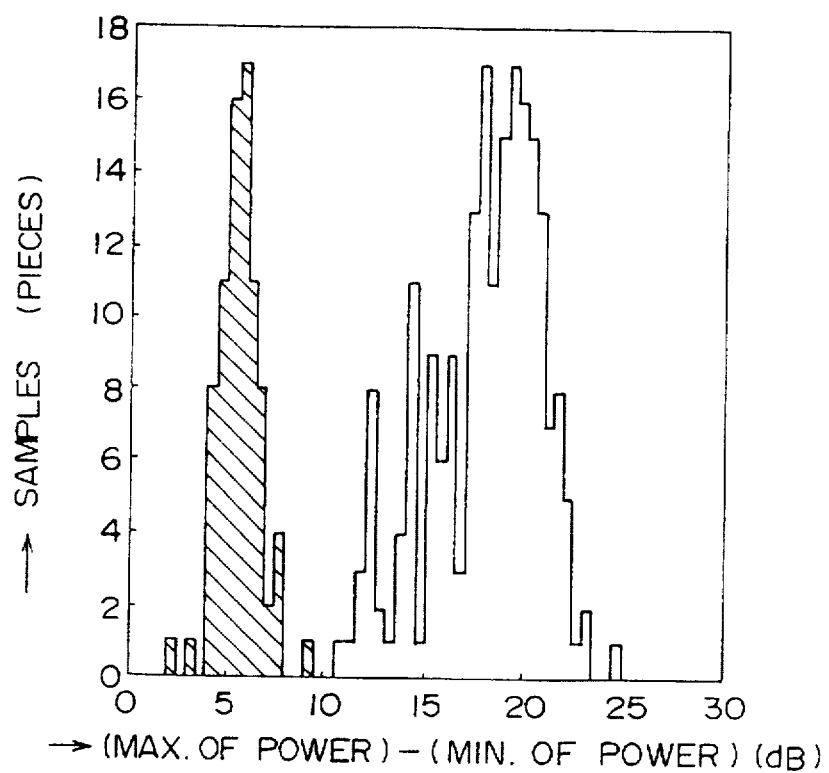
FIG. 6 is a view showing the respective histograms of two statistical variable (maximum-minimum) groups.

FIG. 6 is a view showing the respective histograms of two statistical variable (maximum-minimum) groups one of which is involved in 80 statistical variables extracted in step (e) and another is involved in 200 statistical variables extracted in step (i). In FIG. 6, the axis of abscissas and the axis of ordinates denote values of the statistical variables and the number of samples of the statistical variables each having the associated value, respectively. The slashed portion denotes the statistical variables extracted in step (e). The void portion denotes the statistical variables related to signals including sounds due to the gas leakage, which are extracted in step (i).

As shown in FIG. 6, when the histograms of two statistical variable groups do not overlap with one another, setting up a threshold at the intermediate point makes it possible to determine a leakage of the gas. However, as mentioned above, if there exists a steam trap which causes steam to discharge intermittently in the normal state, the histograms of two statistical variable groups overlap with one another. Thus, in such a case, it is not so easy to set up the threshold.

Figure 7:
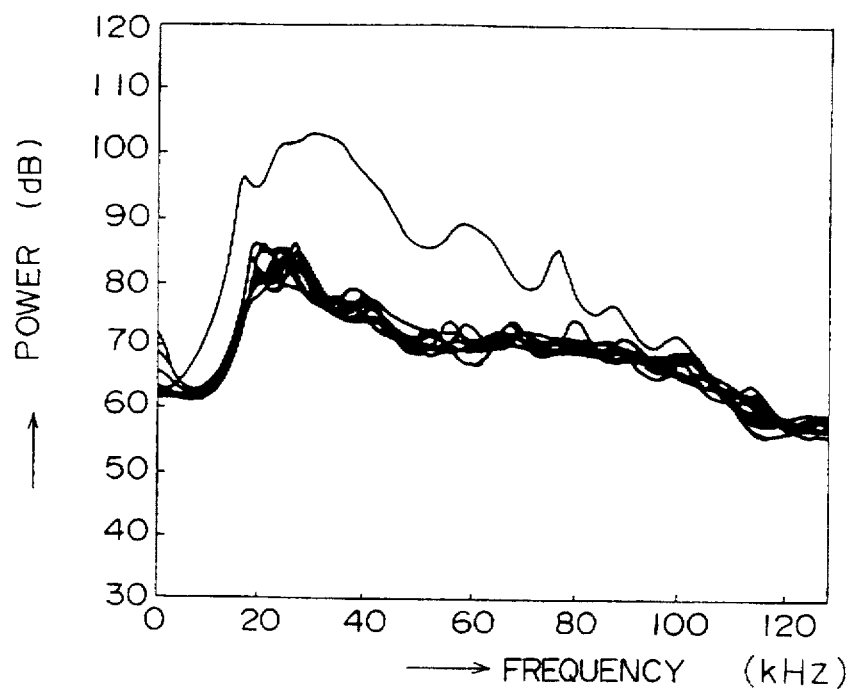
FIG. 7 is a view showing smoothed power spectra of sound signals of each of the pauses formed through partitioning a sound, which is collected in an instant an intermittent leakage due to the steam trap occurs, at fixed intervals of time, at 10-pause correspondence.
Figure 8:
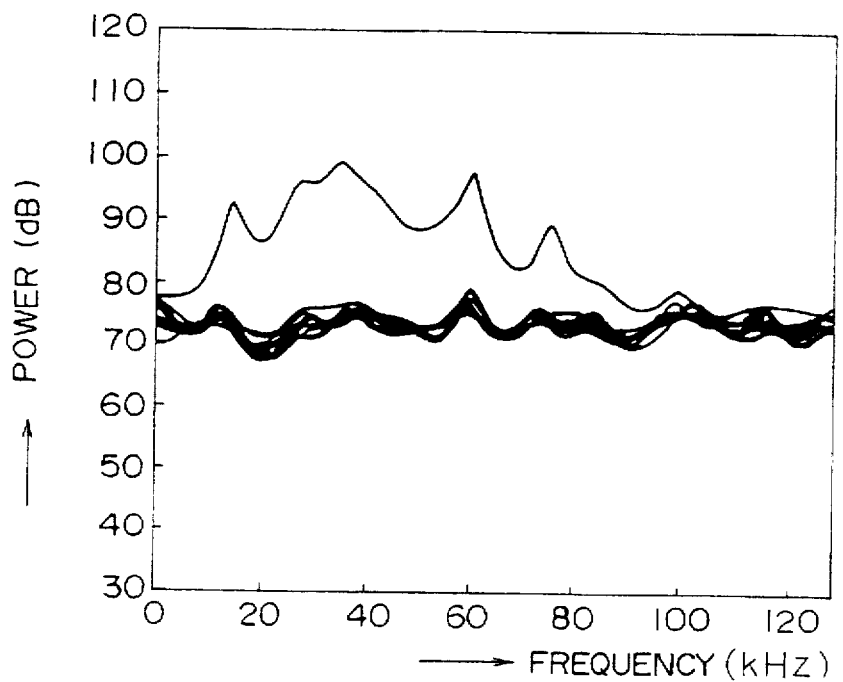
FIG. 8 is a view showing power spectra of residual signals formed by means of letting an inverse filter, which are obtained from signals involved in the background noises only, interact with the sound signals shown in FIG. 7.

FIG. 7 is a view showing smoothed power spectra of sound signals of each of the pauses formed through partitioning a sound, which is collected in an instant an intermittent leakage due to the steam trap occurs, at fixed intervals of time, at 10-pause correspondence. FIG. 8 is a view showing power spectra of residual signals formed by means of letting an inverse filter, which are obtained from signals involved in the background noises only, interact with the sound signals shown in FIG. 7.

Figure 9:
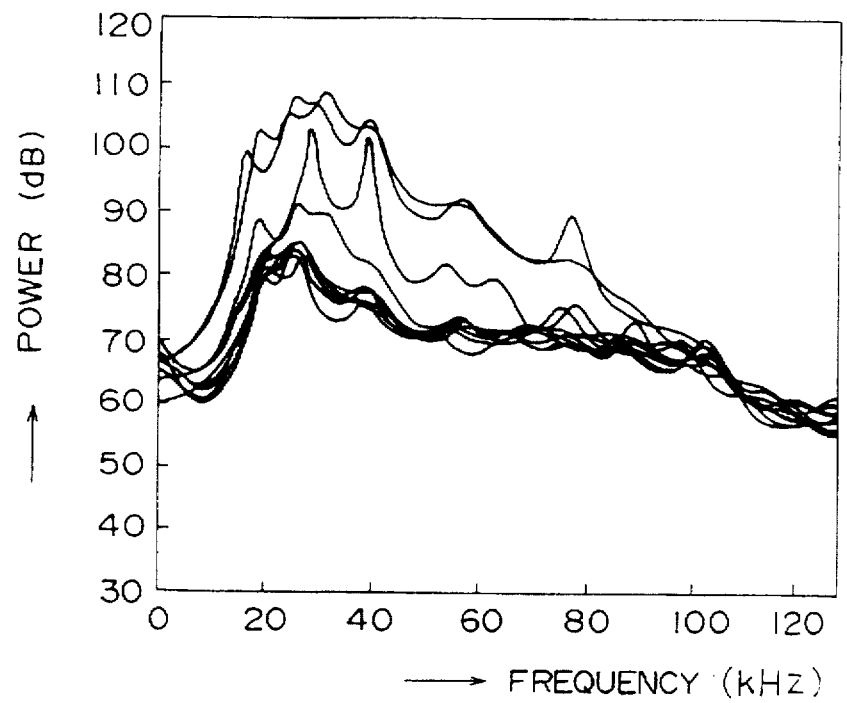
FIG. 9 is a view showing smoothed power spectra of sound signals of each of the pauses formed through partitioning a sound, which is collected in an instant an intermittent leakage due to the steam trap occurs at another occasion, at fixed intervals of time, at 10-pause correspondence.
Figure 10:
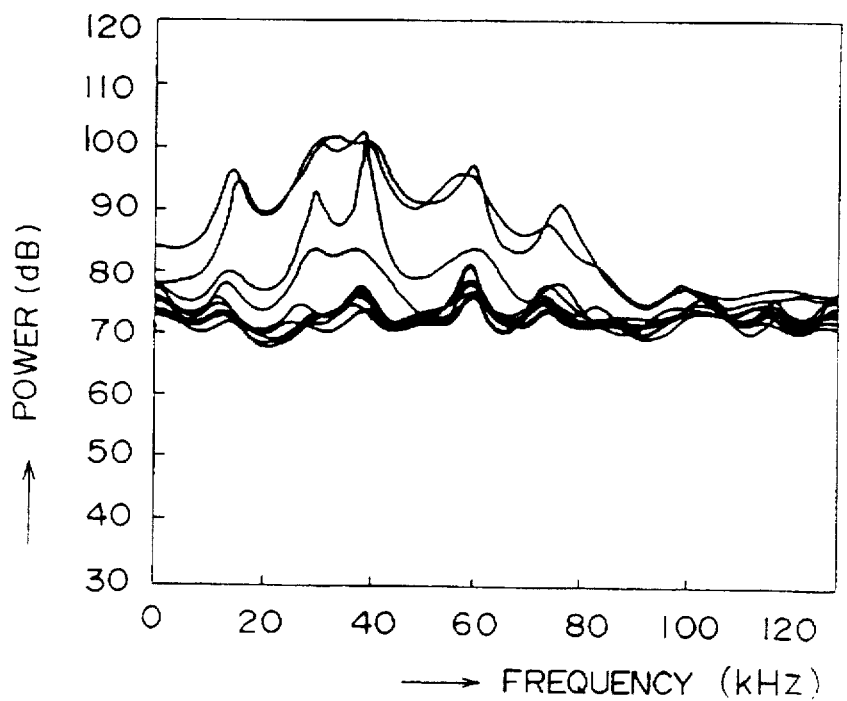
FIG. 10 is a view showing power spectra of residual signals formed by means of letting an inverse filter, which are obtained from signals involved in the background noises only, interact with the sound signals shown in FIG. 9.

FIG. 9 is a view showing smoothed power spectra of sound signals of each of the pauses formed through partitioning a sound, which is collected in an instant an intermittent leakage due to the steam trap occurs at another occasion, at fixed intervals of time, at 10-pause correspondence. FIG. 10 is a view showing power spectra of residual signals formed by means of letting an inverse filter, which are obtained from signals involved in the background noises only, interact with the sound signals shown in FIG. 9.

As will be easily understood from these figures, the statistical variable (maximum-minimum) overlaps in part with the statistical variable (slashed portion in FIG. 6) involved in the existence of an abnormal gas leakage. Thus, in these cases, it would be difficult to expect a great accuracy of decision simply with a simple threshold processing.

In view of the foregoing, according to the present embodiment, in steps (j) to (m), it is determined as to whether a statistical significant difference exists. Thus, it is possible to determine a "normal leakage" due to the steam trap shown in FIGS. 7–10 as "normal" in a similar fashion to that of the noises only, and determine a continuous "abnormal leakage" only as "abnormal".

In this manner, according to the present embodiment, even in a case where there exists a halfway phenomenon between a phenomenon in the normal state and a phenomenon in the abnormal state, it is possible to exactly discriminate normality or abnormality.

Incidentally, according to the present embodiment, both the F-test and the t-test are performed, and as a result, when the significant difference is detected in either one of the F-test and the t-test, the "possible leakage" is determined. However, the determination may be varied in accordance with the application of the present invention. For example, in a case where the existence of the significant difference can be determined in accordance with either one of the F-test and the t-test, it is acceptable to perform only either one of the F-test and the t-test. Further, depending on the applications, it is acceptable that the significant difference is only determined when the significant difference is detected in both the F-test and the t-test. Further, it is acceptable to adopt a statistical test scheme other than the F-test and the t-test. Furthermore, according to the present embodiment, the test of the existence of the significant difference is performed with the level of significance 5%. However, it is possible to perform the test with an optional level of significance in accordance with the object or the application field of the invention. Alternatively, it is acceptable to use a degree of deviations of the variance or the mean value as it is, without performing the test. A technique such that a degree of deviations of the variance or the mean value is used as it is effective in a field of presuming a possibility of occurrence of a malfunction or a failure through a variation of an operating sound of a motor for example as compared with the operating sound in the initial state, but not an application field in which the binary determination such as "leakage present" or "leakage absent" is performed.

Table 1 shows that when artificial defects (holes or slits) in various sizes are formed on an inflammable gas piping in the above-mentioned embodiment so that a gas pressure in the pipe and a distance between a place of collecting a sound and the artificial defect are varied, whether the existence of the defects is properly detected.

TABLE 1

| condition | pressure (MPa) | Distance | | | |
|---|---|---|---|---|---|
| | | 1 m | 2 m | 4 m | 5 m |
| 0.5 mmφ (hole) | 0.1 | — | ○ | ○ | — |
| " | 0.2 | — | ○ | — | — |
| " | 0.4 | — | ○ | — | — |
| 1.0 mmφ (hole) | 0.1 | — | ○ | ○ | ○ |
| " | 0.2 | — | ○ | ○ | ○ |
| " | 0.3 | — | — | ○ | ○ |
| " | 0.4 | — | ○ | ○ | ○ |
| 2.0 mmφ (hole) | 0.1 | — | — | ○ | ○ |
| " | 0.2 | — | — | ○ | ○ |
| " | 0.3 | — | — | ○ | ○ |
| " | 0.4 | ○ | — | ○ | ○ |
| 10 mm × 0.1 mm (slit) | 0.1 | — | — | — | ○ |
| " | 0.2 | — | — | — | ○ |
| " | 0.3 | — | — | — | ○ |
| " | 0.4 | — | — | — | ○ |
| 10 mm × 1.3 mm (slit) | 0.1 | — | — | — | ○ |
| " | 0.2 | — | — | — | ○ |
| " | 0.3 | — | — | — | ○ |
| " | 0.4 | — | — | — | ○ |

In Table 1, the mark "○" denotes that in both a case where only the background noise exists without a leakage and a case where "normal leakage" due to the steam trap exists, they are determined as "normal", and in a case where "abnormal leakage" due to the artificial defects exists, it is determined as "abnormal". The mark "-" denotes that the experiment is not carried out.

According to the above-mentioned embodiment, in step (e), a difference between the maximum and the minimum of the power spectra of the residual signals in the frequency range of 50 KHz–100 KHz is extracted in the form of statistical variable. Also in a case where a difference between the maximum and the minimum of the power spectra of the residual signals in the frequency range of 25 KHz–50 KHz is extracted in the form of statistical variable, in a similar fashion to that of the above, a preferable result can be obtained. Thus, in this manner, it is possible to optionally select the ultrasonic band over the wide range to extract the statistical variable.

Figure 11:
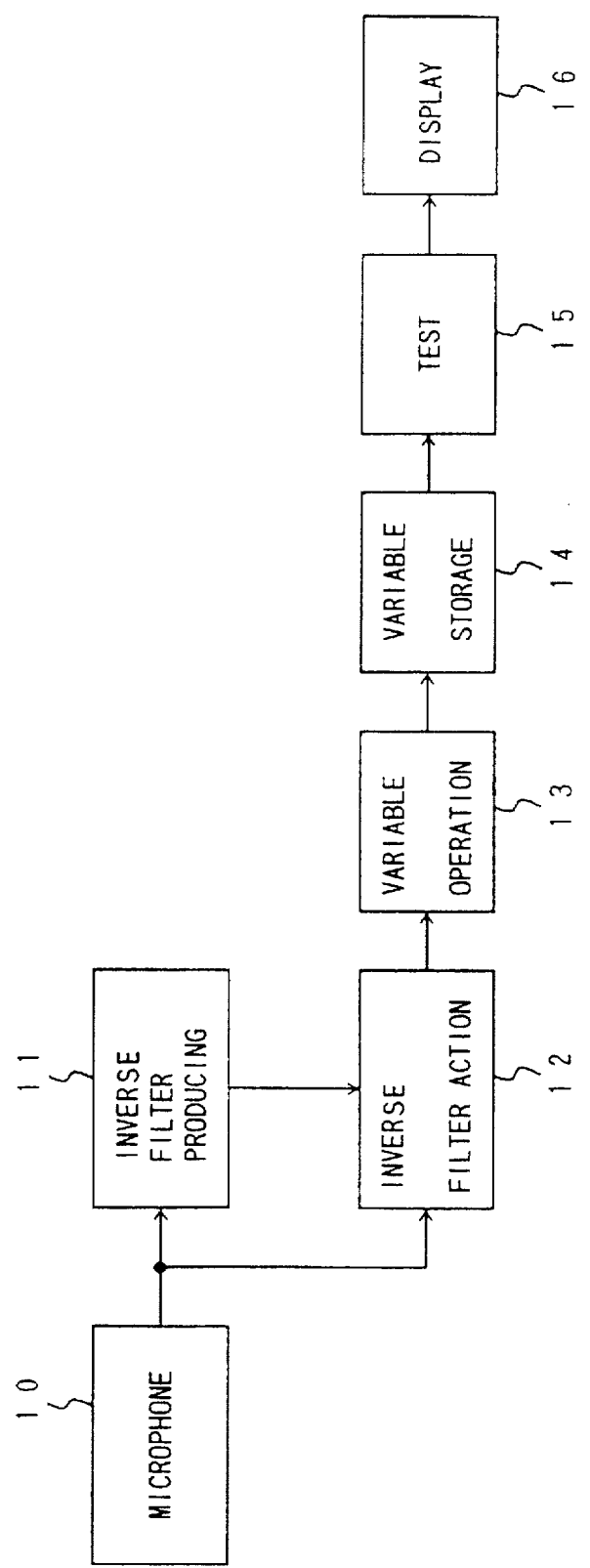
FIG. 11 is a block diagram of one embodiment of the first subject identification apparatus according to the present invention.

FIG. 11 is a block diagram of one embodiment of the first subject identification apparatus according to the present invention. Here, there will be explained a test as to normality or abnormality of inflammable gas piping facilities, using an apparatus shown in FIG. 11.

First, background noises are collected through an ultrasonic microphone 10, and data of the first pause of the background noises are fed to an inverse filter producing unit 11. The inverse filter producing unit 11 produces an inverse filter on the basis of the received background noise data.

The ultrasonic microphone 10 collects subsequently the background noises. The collected background noise data are fed to an inverse filter action unit 12. The inverse filter action unit 12 partitions the received background noise data at fixed intervals of time, and lets the inverse filter produced in the inverse filter producing unit 11 interact with the background noise data on each of the pauses to evaluate the respective residual signals. The respective residual signals, which are produced in the inverse filter action unit 12, are fed to a variable operation unit 13. In the variable operation unit 13, smoothed power spectra of the received residual signals are subjected to the arithmetic operation to extract the maximum and the minimum of the smoothed power spectra in the frequency range of 50 KHz–100 KHz, so that a value (maximum-minimum) is evaluated in the form of the statistical variable.

The statistical variable thus obtained is stored in a variable storage unit 14.

Next, a switch not illustrated is changed over to evaluate a further statistical variable through collection of the sound in a similar fashion to that of the above-mentioned background noises, and the statistical variable thus evaluated is stored in the variable storage unit 14. But, in this case, the inverse filter producing unit 11 does not produce a new inverse filter, and the inverse filter action unit 12 uses the inverse filter, which is involved in the background noises before change over of the switch, as it is.

In this manner, when two statistical variable groups are stored in the variable storage unit 14, those statistical variable groups are supplied to a test unit 15. In the test unit 15, by the F-test and the t-test, it is determined as to whether a statistically significant difference exists between the two statistical variable groups. A result of the tests is displayed on a display unit 16.

Figure 12:
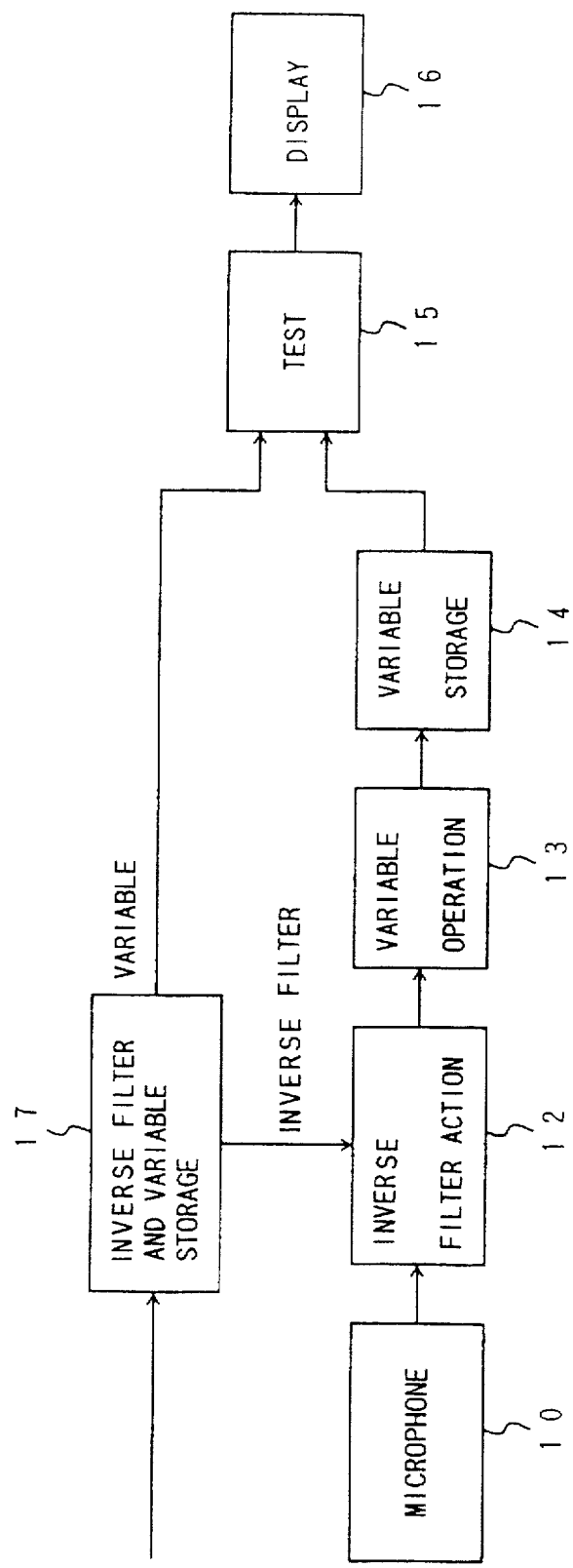
FIG. 12 is a block diagram of one embodiment of the second subject identification apparatus according to the present invention.

FIG. 12 is a block diagram of one embodiment of the second subject identification apparatus according to the present invention. In FIG. 12, the same reference parts as those of FIG. 11 are denoted by the same reference numbers as those of FIG. 11. And only the different points will be explained.

An apparatus shown in FIG. 12 is provided with, instead of the inverse filter producing unit 11 shown in FIG. 11, an inverse filter produced on the basis of background noises and storage unit 17 for storing a statistical variable based on residual signals formed by letting the inverse filter interact with the background noises.

In case of apparatuses having a single function, it is sufficient that the statistical variable involved in the inverse filter and the background noise s is produced once. Accordingly, such a statistical variable is produced by a personal computer and the like not illustrated, and stored in the storage unit 17 of the apparatus shown in FIG. 12.

Incidentally, for example, the arithmetic operations of inverse filter action unit 12 and the variable operation unit 13 may be implemented by the associated exclusive hardware. But, usually, such arithmetic operations are implemented in accordance with a software in a computer system.

Figure 13:
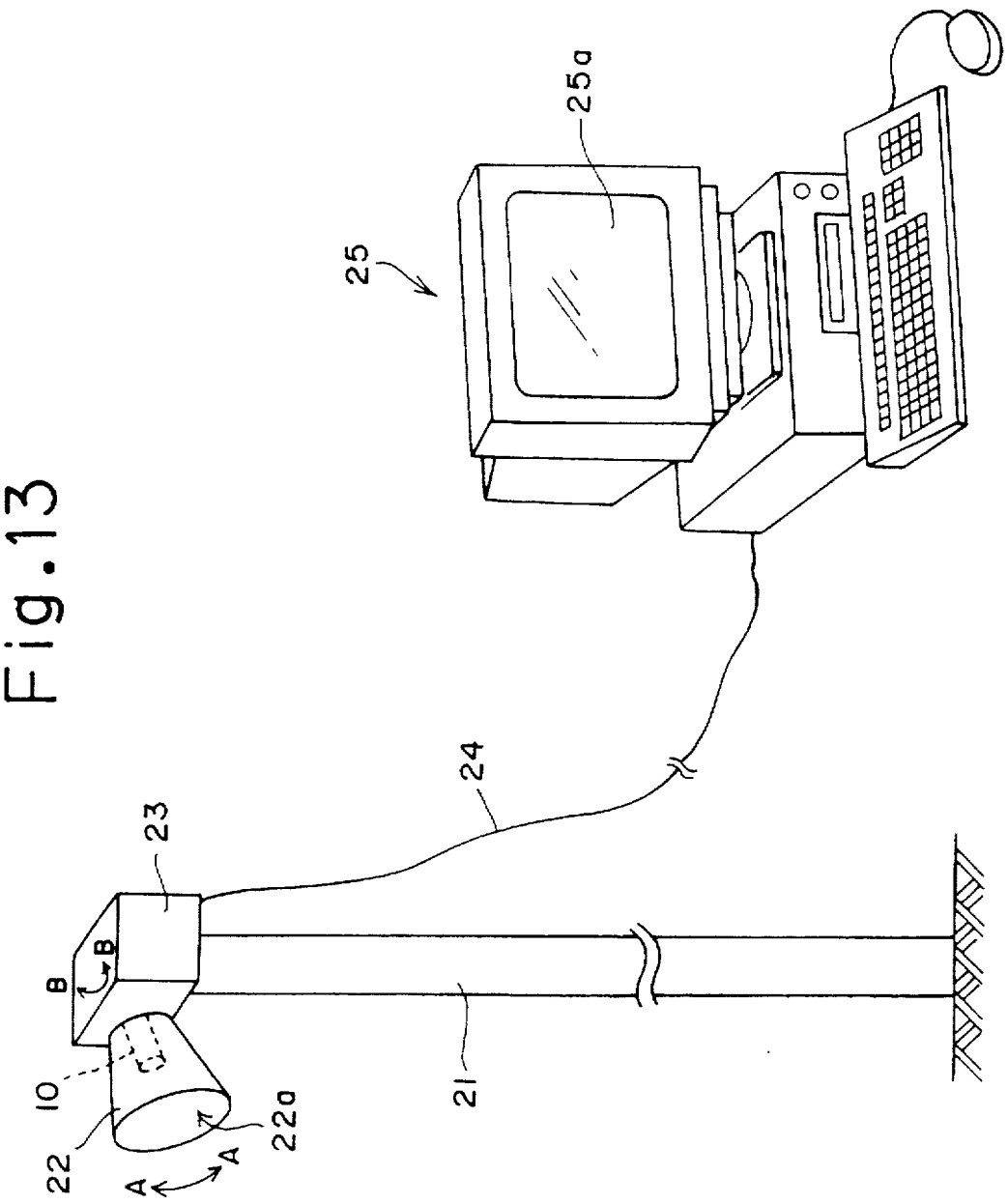
FIG. 13 is a typical illustration of one embodiment of a subject identification system according to the present invention.

FIG. 13 is a typical illustration of one embodiment of a subject identification system according to the present invention.

A pole 21 is installed at one place or a plurality of places (FIG. 13 shows one place only) within a plant having a number of inflammable gas piping facilities. The top of the pole 21 is provided with an ultrasonic microphone 10 for detecting ultrasounds. The ultrasonic microphone 10 is covered with a hood 22 having an opening 22a in the direction to which the tip of the ultrasonic microphone 10 is oriented, so that the ultrasonic microphone 10 receives only a sound emanated from the direction of interest. The ultrasonic microphone 10 with the hood is mounted on an attitude control apparatus 23, so that the ultrasonic microphone 10 is controlled in the direction in the vertical direction (A-A direction in the figure) and the horizontal direction (B-B direction in the figure) in accordance with the attitude control apparatus 23. The attitude control apparatus 23 controls the ultrasonic microphone 10 in the direction on a circulating basis so that the ultrasonic microphone 10 intermittently turn various directions and again an initial direction in accordance with a predetermined sequence.

Ultrasonic signals collected by the ultrasonic microphone 10 are transmitted via a cable 24 to a monitor device 25 constituting of a computer system, which is installed in, for example, a central control room and the like. In the monitor device 25, the functions corresponding to the units 11 to 16 in FIG. 11 are implemented using softwares. The monitor device 25 evaluates, first, in a case where all the pipes in the plant are in the normal state, a statistical variable group as a reference on the basis of the ultrasonic signals collected by the ultrasonic microphone 10 whenever the ultrasonic microphone 10 turns the various directions.

Thereafter, the monitor device 25 enters a monitor state in which a statistical variable group is evaluated, whenever the ultrasonic microphone 10 turns the various directions, by letting the inverse filter interact with the ultrasonic signal associated with each of the directions; a test as to whether a statistical significant difference exists between the statistical variable group thus evaluated and the statistical variable group as a reference is performed; and a test result is displayed on a display screen 25a.

Incidentally, according to the above-mentioned system, while it is explained that the ultrasonic microphone 10 intermittently turns the various directions, it is acceptable that the ultrasonic microphone 10 continuously turns the various directions.

The above-mentioned embodiments relate to an example in which sounds (ultrasounds) are collected and it is tested whether a significant difference exists between sound-to-sound. However, it should be noted that the physical amount of interest in the present invention is not restricted to sounds such as ultrasounds or the like, and is applicable to any physical amounts. Further, the above-mentioned embodiments relate to an example in which the present invention is applied to a test for the presence or absence of the leakage on the inflammable gas piping. However, the present invention is not restricted in the subject, and has an extensive application field.

What is claimed is:

1. A subject identification method comprising:
    a first step of obtaining a plurality of first time sequential signals each carrying a predetermined physical amount from a predetermined first subject;
    a second step of producing an inverse filter on the basis of at least one of said plurality of first time sequential signals;
    a third step of evaluating a plurality of first residual signals by means of letting said inverse filter interact with at least part of said plurality of first time sequential signals;
    a fourth step of evaluating a plurality of predetermined statistical variables on the basis of said plurality of first residual signals;
    a fifth step of obtaining a plurality of second time sequential signals each carrying said predetermined physical amount from a predetermined second subject;
    a sixth step of evaluating a plurality of second residual signals by means of letting said inverse filter interact with said plurality of second time sequential signals;

a seventh step of evaluating said plurality of predetermined statistical variables on the basis of said plurality of second residual signals; and an eighth step of presuming or testing, using a technique of a statistical test, a statistical difference between the plurality of predetermined statistical variables evaluated in the fourth step and the plurality of predetermined statistical variables evaluated in the seventh step.

2. A subject identification method according to claim 1, wherein the fourth step has a step of evaluating power spectra of a frequency band of at least part of said plurality of first residual signals, and an additional step of evaluating the predetermined statistical variables on the basis of the power spectra, and wherein the seventh step has a step of evaluating power spectra of a frequency band of at least part of said plurality of second residual signals, and an additional step of evaluating the predetermined statistical variables on the basis of the power spectra.

3. A subject identification method according to claim 1 or 2, wherein the eighth step is to presume or test a difference in population variances and/or population means.

4. A subject identification method according to claim 1 or 2, wherein the first and second subjects are the same or same type of subject.

5. A subject identification method according to claim 3, wherein the first and second subjects are the same or same type of subject.

6. A subject identification method according to claim 1, wherein said eighth step is of presuming or testing the statistical difference using a technique of a statistical test including an F-test.

7. A subject identification method according to claim 1, wherein said eighth step is of presuming or testing the statistical difference using a technique of a statistical test including a t-test.

8. A subject identification apparatus comprising:

a sensor for obtaining time sequential signals carrying a predetermined physical amount by means of measuring the predetermined physical amount of a subject;

an inverse filter producing means for producing an inverse filter on the basic of the time sequential signals obtained by said sensor;

a variable operating means for evaluating residual signals by means of letting said inverse filter produced by said inverse filter producing means interact with the plurality of time sequential signals obtained by the sensor, and evaluating predetermined statistical variables on the basis of the residual signals;

a storage means for storing the predetermined statistical variables evaluated by said variable operating means; and a statistical means for presuming or testing, using a technique of a statistical test, a statistical difference between group in which the plurality of predetermined statistical variables stored in said storage means are partitioned into at least two groups.

9. A subject identification apparatus according to claim 8, wherein said statistical means presumes or tests the statistical difference using a technique of a statistical test including an F-test.

10. A subject identification apparatus according to claim 8, wherein said statistical means presumes or tests the statistical difference using a technique of a statistical test including a t-test.

11. A subject identification apparatus comprising:

a first storage means for storing an inverse filter and a plurality of predetermined statistical variables;

a sensor for obtaining time sequential signals each carrying a predetermined physical amount by means of measuring the predetermined physical amount of a subject;

a variable operating means for evaluating residual signals by means of letting said inverse filter stored in said first storage means interact with the time sequential signals obtained by the sensor, and evaluating the predetermined statistical variables on the basis of the residual signals;

a second storage means for storing the predetermined statistical variables evaluated by said variable operating means; and a statistical means for presuming or testing, using a technique of a statistical test, a statistical difference between the plurality of predetermined statistical variables stored in said first storage means and the plurality of predetermined statistical variables stored in said second storage means.

12. A subject identification apparatus according to claim 11, wherein said statistical means presumes or tests the statistical difference using a technique of a statistical test including an F-test.

13. A subject identification apparatus according to claim 11, wherein said statistical means presumes or tests the statistical difference using a technique of a statistical test including a t-test.

14. A subject identification system comprising:

at least one sound pressure sensor disposed at a place having a predetermined position relation with respect to a subject;

a sensor attitude control apparatus for causing said sound pressure sensor to turn various directions; and a monitor apparatus having an inverse filter producing means for producing an inverse filter on the basis of sound signals obtained by said sound pressure sensor, a variable operating means for evaluating residual signals by means of letting said inverse filter produced by said inverse filter producing means interact with the plurality of sound signals obtained by said sound pressure sensor, and evaluating predetermined statistical variables on the basis of the residual signals, a storage means for storing the predetermined statistical variables evaluated by said variable operating means, and a statistical means for presuming or testing, using a technique of a statistical test, a statistical difference between groups in which the plurality of predetermined statistical variables stored in said storage means are partitioned into at least two groups.

15. A subject identification system according to claim 14, wherein said statistical means presumes or tests the statistical difference using a technique of a statistical test including an F-test.

16. A subject identification apparatus according to claim 14, wherein said statistical means presumes or tests the statistical difference using a technique of a statistical test including a t-test.

* * * * *